(12) United States Patent
Requardt

(10) Patent No.: US 8,874,191 B2
(45) Date of Patent: Oct. 28, 2014

(54) METHOD AND MAGNETIC RESONANCE DEVICE FOR GRAPHICALLY ASSISTING NAVIGATION OF AN INSTRUMENT

(75) Inventor: Martin Requardt, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 620 days.

(21) Appl. No.: 12/833,152

(22) Filed: Jul. 9, 2010

(65) Prior Publication Data

US 2011/0015516 A1 Jan. 20, 2011

(30) Foreign Application Priority Data

Jul. 17, 2009 (DE) .......................... 10 2009 033 676

(51) Int. Cl.
*A61B 5/05* (2006.01)
*A61B 5/06* (2006.01)
*A61B 5/055* (2006.01)

(52) U.S. Cl.
CPC .. *A61B 5/055* (2013.01); *A61B 5/06* (2013.01)
USPC ............................ 600/411; 600/410; 600/424

(58) Field of Classification Search
None
See application file for complete search history.

(56) References Cited

U.S. PATENT DOCUMENTS

| | | | | |
|---|---|---|---|---|
| 5,271,400 A | * | 12/1993 | Dumoulin et al. | ............ 600/410 |
| 5,447,156 A | * | 9/1995 | Dumoulin et al. | ............ 600/419 |
| 5,638,819 A | * | 6/1997 | Manwaring et al. | .......... 600/424 |
| 6,169,917 B1 | * | 1/2001 | Masotti et al. | ................ 600/407 |
| 6,289,233 B1 | * | 9/2001 | Dumoulin et al. | ............ 600/410 |
| 6,346,940 B1 | * | 2/2002 | Fukunaga | ..................... 345/427 |
| 6,470,207 B1 | * | 10/2002 | Simon et al. | ................... 600/426 |
| 6,731,966 B1 | * | 5/2004 | Spigelman et al. | ........... 600/407 |
| 6,733,458 B1 | * | 5/2004 | Steins et al. | ................... 600/461 |
| 6,892,090 B2 | * | 5/2005 | Verard et al. | ................... 600/424 |
| 2002/0110216 A1 | * | 8/2002 | Saito et al. | ........................ 378/19 |
| 2002/0140709 A1 | * | 10/2002 | Sauer et al. | .................... 345/633 |
| 2004/0034297 A1 | | 2/2004 | Darrow et al. | |
| 2004/0044279 A1 | * | 3/2004 | Lewin et al. | ................... 600/407 |
| 2005/0245810 A1 | | 11/2005 | Khamene et al. | |
| 2006/0247520 A1 | * | 11/2006 | McGee | .......................... 600/434 |
| 2008/0081982 A1 | | 4/2008 | Simon et al. | |
| 2012/0089008 A1 | * | 4/2012 | Strehl et al. | ................... 600/411 |

* cited by examiner

*Primary Examiner* — Long V. Le
*Assistant Examiner* — Bradley Impink
(74) *Attorney, Agent, or Firm* — Schiff Hardin LLP

(57) ABSTRACT

In a method and magnetic resonance device for graphically assisting the navigation of an instrument (in particular a medical instrument such as a needle and/or a guide sleeve guiding a needle) within a procedure region of a target subject (in particular a patient), coordinates of a target position and/or target region to be addressed that are obtained from a high-contrast image data set acquired with the magnetic resonance device. Low-contrast image data showing the instrument are acquired continuously and/or intermittently during the navigation and/or the position and orientation of the instrument is determined (in particular measured) with a position determination device. The low-contrast image later are brought into registration with the magnetic resonance device continuously and/or intermittently during the navigation. A representation showing at least the relative position and orientation of the instrument relative to the target position and/or target region is generated and displayed under consideration of the coordinates and the low-contrast image data and/or the position and orientation of the instrument.

11 Claims, 3 Drawing Sheets

METHOD AND MAGNETIC RESONANCE DEVICE FOR GRAPHICALLY ASSISTING NAVIGATION OF AN INSTRUMENT

BACKGROUND OF THE INVENTION

1. Field of the Invention

The present invention concerns a method for graphically assisting the navigation of an instrument (in particular a medical instrument, in particular a needle and/or a guide sleeve guiding a needle) within a procedure region of a target object (in particular a patient) using a magnetic resonance device, wherein coordinates of a target position and/or target region that is to be accessed are obtained from a high-contrast image data set acquired with the magnetic resonance device. The invention additionally concerns an associated magnetic resonance device.

2. Description of the Prior Art

Minimally invasive procedures, primarily in the field of medicine, are implemented with increasing frequency within a magnetic resonance device. Magnetic resonance is superbly suitable for examination planning since it offers the advantage of a very good soft tissue contrast, such that anatomical features (for example blood vessels or nerves) can also be addressed in the procedure planning, in particular the planning of a puncture channel with a needle. For this purpose, it is known to execute a three-dimensional high-contrast acquisition, in order to acquire a high-contrast image data set from which both coordinates of a target position and/or target region to be addressed can be obtained, and the remaining planning of the procedure can ensue; for example, using a procedure with a needle. This planning is for the purpose of designating the point on the skin on the patient at which the needle should be inserted, the angle at which it is to be introduced, and the defined distance by which the needle is to be displaced.

In spite of the poor accessibility in a magnetic resonance device where the patient is supported in the isocenter inside the patient receptacle, this modality, due to the cited advantages, has an increasing popularity. There, however, is a further disadvantage of magnetic resonance imaging. Fast imaging, as is required for a real-time representation of the needle (or a guide sleeve, for example), has only a poor soft tissue contrast, resulting in low-contrast image data. Although the needle can be clearly shown with such a fast imaging (which, for example, shows the feed of a needle—for example a biopsy needle—with three images per second), the contrast at the target position/target region is no longer sufficient.

To solve this problem, it has been suggested to regularly interrupt the procedure in order to interpose a high-contrast scan that then allows the assessment of whether the target position or, the target region is hit. However, this extends the procedure and entails the risk of patient movement.

SUMMARY OF THE INVENTION

An object of the invention is to provide a method for graphically assisting the navigation of an instrument (in particular a needle or a guide sleeve guiding a needle) with which a user can obtain information as quickly as possible (in particular in real time) as to how the instrument should be navigated further in order to reach the target position and/or the target region.

To achieve this object in a method of the aforementioned type, according to the invention low-contrast image data showing the instrument are acquired continuously and/or intermittently during the navigation and/or the position and orientation of the instrument is determined (in particular measured) via a position determination device registered with the magnetic resonance device continuously and/or intermittently during the navigation, and a presentation showing at least the relative position and orientation of the instrument relative to the target position and/or target region is generated and displayed under consideration of the coordinates and the low-contrast image data and/or the position and orientation of the instrument.

The method according to the invention thus utilizes the fact that the coordinates of the target position and/or target region that is to be addressed are defined as precisely as permitted by the low-contrast image data and/or the data of the position determination device. It is therefore possible to generate a representation from which at least the relative position of the target position and/or target region relative to the instrument (in particular the needle) can be ascertained. It is particularly advantageous that the representation can be generated extremely quickly (due to the registration that is already present) so that tracking of the instrument and its relative position relative to the target position and/or target region can ensue in real time. A person implementing the procedure thus receives important and intuitively comprehensible information and can specifically address the target region and/or target position in spite of the difficult access in a magnetic resonance device.

In order to obtain the position and orientation of the instrument as quickly as possible, the method according to the invention makes use of two variants, that can also be used cumulatively. As has already been mentioned, techniques are known with which low-contrast image data can be acquired with a frequency of at least one image per second (for example three images per second) via virtual fluoroscopic imaging. A slice in which the instrument is located is thereby typically acquired. Techniques are also known which acquire multiple low-contrast images, for example methods in which one or two slices are initially acquired in which the cross section of the instrument (but in particular of a guide sleeve) is detected, whereupon the next actual measurement slice can then be acquired so that it lies in the same plane as the instrument. In principle, where the instrument is located and the direction it is pointing in space can be recognized in the low-contrast image data.

Another variant is the use of a position determination device, wherein (for example) acquisition coils at the instrument can be provided with which the bearing of the instrument in space can be detected. Naturally, other position determination systems can also be used that are widely known in the prior art and do not need to be presented here. Such a position determination device has been brought into registration with the magnetic resonance device (for example by a calibration procedure) so that the measurement of the position and orientation of the instrument can ensue directly in coordinates of the magnetic resonance device. For example, in this case the basis of the representation to be generated can be formed by the high-contrast image data set.

In a further embodiment of the method, the representation is a symbolic marking indicating the location/orientation of the target position and/or target region. A symbol that indicates where the target position and/or target region is located is consequently incorporated so that the navigation can be oriented on this symbol.

The representation can be a slice image of the low-contrast image data, wherein the marking has already been inserted into the slice image in the reconstruction of this slice image. Since the coordinates of the target position and/or target region are already present in the coordinate system of the magnetic resonance device, thus in the same coordinate system in which the low-contrast image data (here the slice image) are acquired, the symbolic marking can already be inserted into the slice image when this slice image is reconstructed. Additional image processing is thus no longer necessary; rather, a slice image is directly created from which the bearing of the target position and/or target region is already to be learned. This slice image can then be used and displayed immediately as a representation, such that significant time is saved and therefore the person implementing the procedure is provided with the relevant information more quickly.

In addition to the marking, the representation can be an instrument marking reflecting the position and orientation of the instrument. If a position determination device is used, the position and orientation of the instrument is ultimately detected, such that this can then be graphically copied into the representation. It is possible to use only a graphic that shows the instrument and its spatial relationship to the target position/target region as a measurement result (consequently as a representation).

In a further embodiment of the present invention, the marking is information about the bearing and/or the distance of the target position and/or target region perpendicular to the slice plane in addition to the two-dimensional position of the target position and/or target region in the displayed slice (corresponding to the slice of the slice image and/or defined by at least a part of the instrument). A plane is thus shown in the two-dimensional representation, or is defined by the current bearing of the instrument (in particular the needle). For example, a plane in which the needle lies can be selected, or even a plane in which the needle and the target position and/or target region lie. The marking now shows not only how the target position and/or target region lies as projected on the slice but also whether and possibly to what extent it lies above or below the slice. In the manner of the marking it can thus be intuitively recognized by the user whether the needle is located in the correct slice plane and in which direction the deviation is present. The location of the target position and/or target region within the slice, above the slice or below the slice can be indicated by the shape and/or the color of the marking, and/or the distance of the target position and/or target region from the slice can be indicated by the size of the marking. For example, a star can indicate that the target position and/or target region is located in the shown slice, a square can indicate that the target position and/or target region lies above the slice, and a circle can be used for target positions and/or target regions below the shown slice. The edge length of the square or the diameter of the circle can then scale with the distance perpendicular to the slice plane, for example. A classification into distance classes is also possible. It is thus very quickly and intuitively communicated to the user how he or she must conduct the further navigation of the instrument.

The low-contrast image data can be two slice images (in particular two slice images essentially perpendicular to one another), wherein a representation of each slice image is generated and displayed. For example, two-plane projection techniques can be used that display the projection of the instrument and additionally graphically indicate the target position and/or target region in two different planes. In this manner a three-dimensional position can ultimately be communicated that provides the party implementing the procedure with additional information.

Furthermore, at least one additional subject and/or area whose coordinates in the high-contrast image data set are known can be incorporated into the representation. The examination planning and post-processing of a high-contrast image data set can comprise not only the establishment of the target position and/or target region; rather, it can additionally be possible that additional marking processes are contained. For example, organs can be segmented and defined in terms of their bearing. This information is likewise present in the coordinates of the magnetic resonance device and can consequently be integrated into the representation without a larger time loss. This is particularly advantageous if an abstract graphic is present. For example, if a tumor in the prostate should be treated, the prostate can also be incorporated into a purely graphical representation in addition to the position and orientation of the instrument and the target position/target region.

In a further embodiment of the method according to the invention, at least one future position and/or a movement line is determined from the position and orientation of the instrument and incorporated into the representation. If the location of the instrument is known first, in the case of a needle (for example) it can be determined in advance how the needle channel would proceed further. In particular, it is then up to the user to recognize whether the needle channel will actually hit the target position and/or target region. If the position and orientation of the instrument are known, such an assistance can be determined promptly and very quickly and can further increase the intuitive comprehensibility of the representation.

In addition or as an alternative to a future position and/or a movement line, additional geometric parameters (in particular a deviation from the target position and/or target region and/or a corrected orientation and/or movement line) can also be determined and incorporated into the representation. Ultimately, as long as the parameter is to be determined quickly and inserted into the representation, any additional geometric information that can be concluded from the relative position of target position/target region and instrument can be provided to the user in the representation.

In addition to the method, the present invention also concerns a magnetic resonance device having a control device fashioned to execute the method according to the invention. The magnetic resonance device according to the invention is thus suitable to continuously and/or intermittently acquire low-contrast image data showing the instrument during the navigation (in particular based on a special, fast measurement protocol) and/or comprises a position determination device registered with the magnetic resonance device, via which position determination device the position and orientation of an instrument (in particular a medical instrument, for example a needle) can be determined. Under consideration of coordinates of a target position and/or target region that is to be addressed (which coordinates are obtained with the use of a high-contrast image data set), the control device is additionally fashioned to generate and to display a representation showing the relative position and orientation of the instrument relative to the target position and/or target region, for which a suitable display (for example a monitor) is provided.

The magnetic resonance device according to the invention thus represents a highly suitable means to implement minimally invasive procedures on a patient located in the patient receptacle, for example procedures with a needle guided in a guide sleeve. Due to the generation and display of the representation, a very current imaging that advantageously supports the navigation can be intuitively provided to the user.

The control device particularly can include a reconstruction unit to reconstruct slice images (in particular also from low-contrast image data) which is also fashioned to insert a symbolic marking indicating the position of the target position and/or target region into the slice image during the reconstruction of said slice image. An external image post-processing is thus no longer necessary in order to generate the representation. The additional embodiments of the method according to the invention can naturally also be analogously transferred to the magnetic resonance device according to the invention.

DESCRIPTION OF THE PREFERRED EMBODIMENTS

Figure 1:
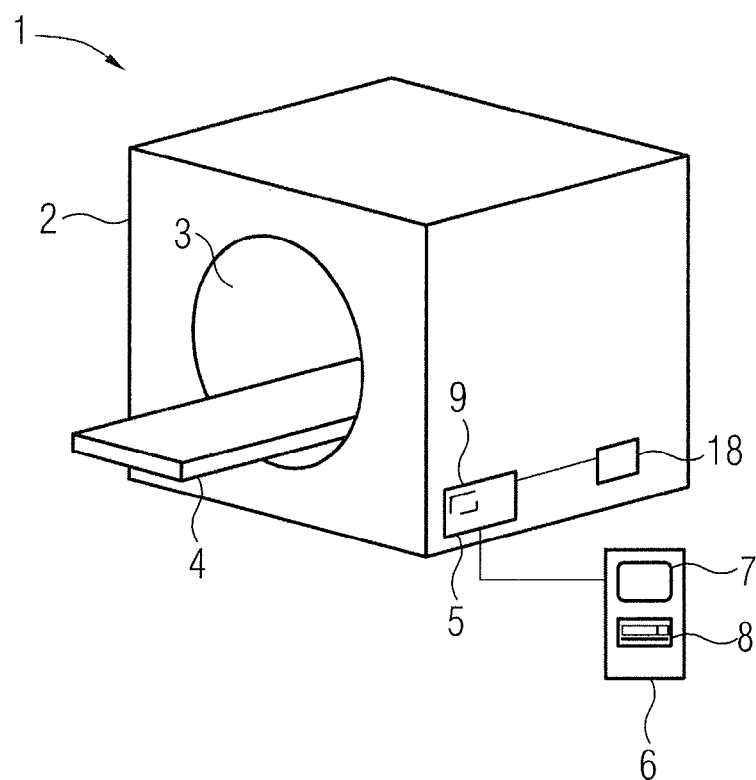
FIG. 1 schematically illustrates a magnetic resonance device according to the invention.

FIG. 1 shows a magnetic resonance device 1 according to the invention. It comprises (the manner is fundamentally known) a magnetic arrangement 2 in which, gradient coils and radio-frequency coils are provided in addition to the basic field magnet. The function and the interaction of these components is widely known and does not need to be presented in detail here. The magnet arrangement 2 has a patient receptacle into which a patient can be driven by means of a patient bed 4.

The operation of the magnetic resonance device 1 is controlled by a control device 5 that is fashioned for the implementation of the method according to the invention for graphically assisting the navigation of a medical instrument within a procedure area of a patient. The magnetic resonance device 1 also includes a display and operating unit 6 that comprises a display unit 7 (for example a monitor) and an input on it 8 (for example a mouse, a keyboard or the like).

In the following the method according to the invention is explained in detail using the example of a minimally invasive procedure with a needle (for example a biopsy needle) directed in a guide sleeve in the region of the prostate of a patient. After a patient has first been inserted beforehand into the patient receptacle 3, a high-contrast image data set (in particular a three-dimensional high-contrast image data set) is acquired that serves for the procedure planning. Coordinates of a target region (for example a tumor) are initially determined in said high-contrast image data set so that the bearing of the target region is clearly defined in the coordinate system of the magnetic resonance device 1. In addition to this, the point at which the needle should be introduced, the insertion angle and the puncture channel are also frequently planned in this phase of the procedure planning.

Due to the difficult accessibility to the patient in the magnetic resonance device 1 (naturally the patient should not be moved relative to the high-contrast exposure), a graphical assistance is extremely helpful for the monitoring of the actual navigation of the needle in the patient. Such a graphical assistance is provided by the method according to the invention, which should initially be described in a first embodiment in which low-contrast image data form the basis of the representation.

During the navigation (thus the actual procedure), low-contrast image data showing the needle are thereby continuously acquired. In this exemplary embodiment it is thereby provided to initially acquire two slice images in which the cross section of the needle and/or the guide sleeve can be located in order to finally place the third, actual slice image so that it lies in the plane of the needle itself so that it is possible to acquire one slice image per second in the plane of the needle. This slice image is reconstructed in a reconstruction unit 9 of the control device 5, wherein this in turn ensues in the coordinate system of the magnetic resonance device. That means that where the target region lies is already known in the reconstruction. During the reconstruction it is therefore already provided to incorporate a symbolic marking that indicates the bearing of the target region (here the tumor) into the slice image. A representation using which the relative bearing of needle and tumor is easily and intuitively apparent is thus created in a simple manner.

Figure 2:
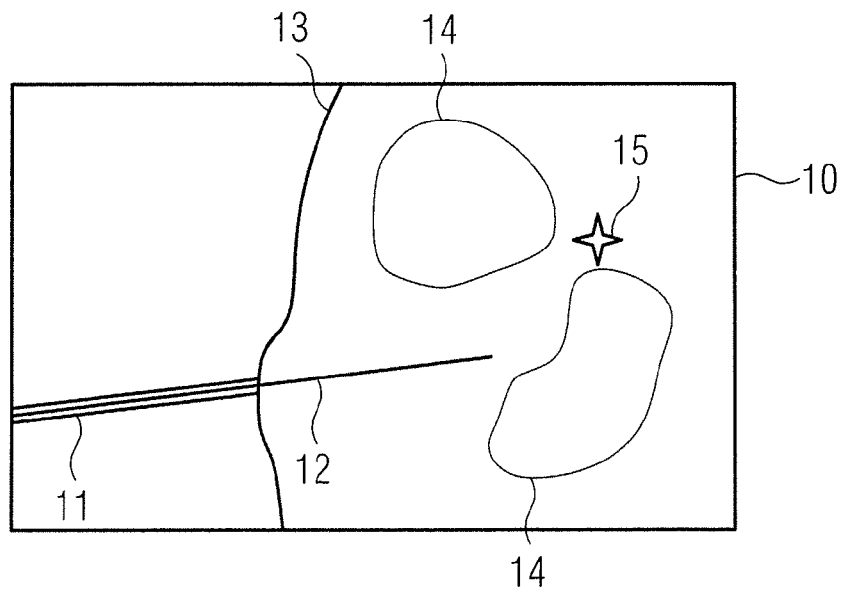
FIG. 2, FIG. 3 and FIG. 4 respectively show various representations in a first embodiment of the method according to the invention.
Figure 3:
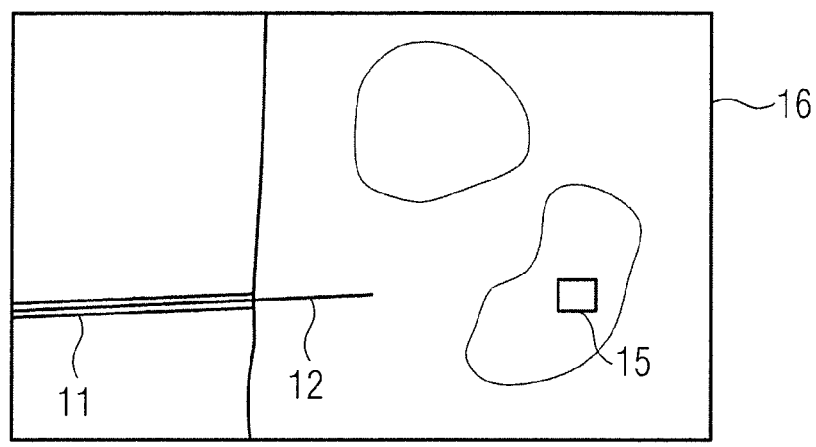
Figure 4:
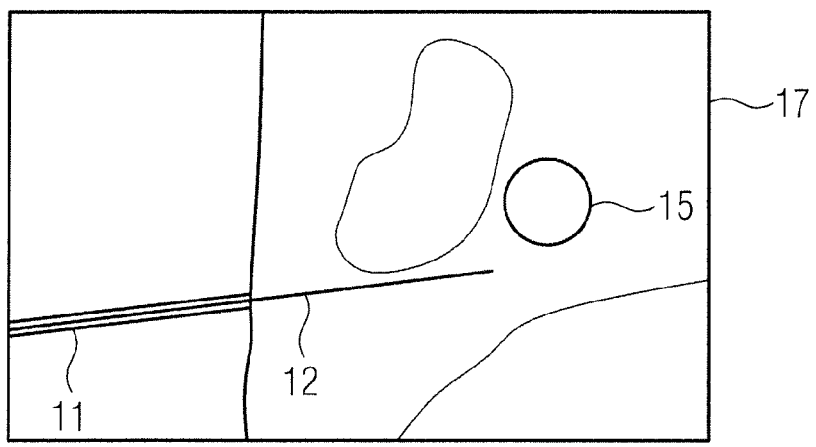

FIGS. 2-4 show different representations for different configurations as they can be shown on the display means 7, for example. The representations (which are a slice image of the low-contrast data) are shown here in abstract form.

FIG. 2 shows a first possible representation 10. The guide sleeve 11 and the needle 12 are clearly recognizable in the slice image, wherein the guide sleeve 11 is placed on the surface of a patient. Other structures 14 are also roughly recognizable in the low-contrast data of the slice image. However, this does not apply for the target region, namely the tumor. This was therefore already inserted in the form of a marking 15 (here a star) in the reconstruction of the slice image. The shape of the marking 15 as a star indicates that the tumor is located in the slice plane of the shown slice image.

From the representation 10, a party implementing the procedure can consequently clearly recognize that the needle 12 is located in the correct plane; however, the marking 14 was still absent in this plane. He can therefore make corresponding adjustments.

The representation 16 in FIG. 3 shows another configuration. Although there the needle 12 appears to point directly towards the marking 15 (here a square), the shape of the marking 15 as a square indicates that the target region is actually located above the slice plane of the shown slice. The user can accordingly makes an adjustment.

Finally, FIG. 4 shows an additional possible representation 17 in which the marking 15 is formed by a circle with a large diameter. The diameter of the circle thereby represents a measure of the distance at which the target region (here the tumor) is located; the circle itself indicates that the tumor is located below the shown slice plane. An easy correction of the needle 12 in the slice plane is consequently presently necessary, such as a clear downward correction.

Other variations of the marking 15 are also possible in order to depict the bearing of the target region relative to the slice plane as intuitively as possible. For example, colors can be used in order to indicate the bearing above, below or in the slice, as well as characters (for example "+" or "−") contained in the marking. The distance from the slice can also be shown via a color scale or even indicated characters (for example numbers). Various possibilities are conceivable here.

Figure 5:
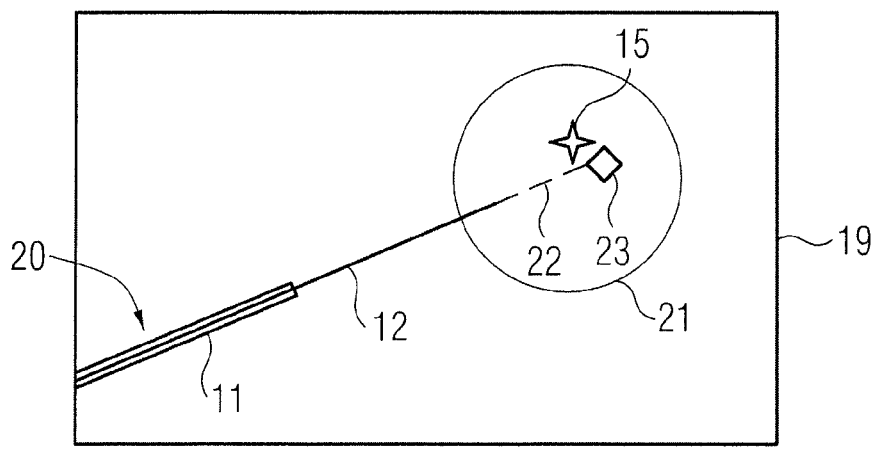
FIG. 5 is a first representation of a second embodiment of the method according to the invention.
Figure 6:
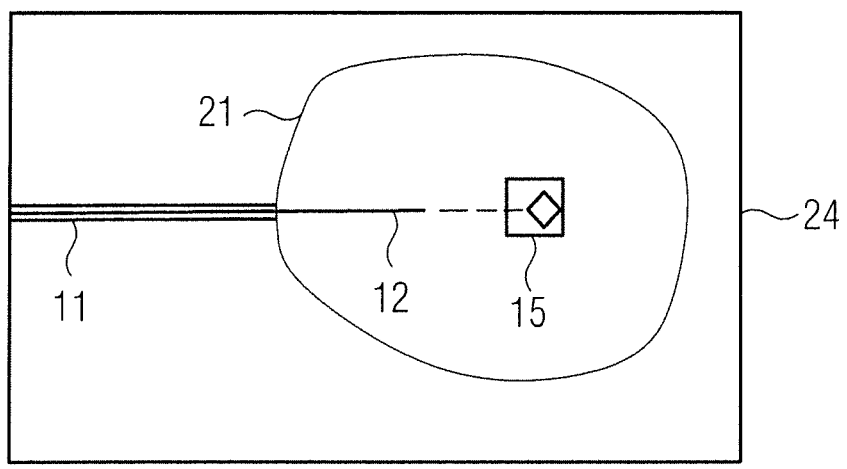
FIG. 6 is a second representation showing a different plane within the scope of the second embodiment of the method according to the invention.

In a second embodiment of the method according to the invention a position determination device 18 is brought into registration with the magnetic resonance device 1 is used in order to determine the position and orientation of the needle in the coordinate system of the magnetic resonance device 1. Furthermore, coordinates of an additional subject (here the prostate, which was segmented in preparation) are also used in this exemplary embodiment. A graphical representation 19 (for example as it is shown in FIG. 5) can then be generated. The needle 12 and the guide sleeve 11 are again recognizable as abstracted graphics 20 in the representation. An additional graph represents the prostate 21 in which again the marking 15 is visible, here a star that indicates that the tumor is located in the shown slice. The slice shown here thereby results from the orientation of the needle 12 in space: it is selected so that the needle 12 lies in this slice plane.

The representation 19 also includes a movement line 22 (displayed as a dashed line in a different color) of the needle 12 and a future position 23 of the tip of the needle 12.

In the second exemplary embodiment of the method according to the invention that is described here, however, a second representation 24 that displays a slice or, respectively, slice plane that is perpendicular to that of the representation 19 is simultaneously generated and displayed in addition to said representation 19. The marking 15 in this second representation 19 clearly corresponds to a square with relatively small edge length, which indicates that the tumor is located somewhat above this slice plane.

Even more information can thus be provided to the user.

Such a representation in two planes is also advantageously conceivable in the first exemplary embodiment of the method according to the invention, in which slice images form the basis of the representation. For example, two slice images standing perpendicular to one another can thus be acquired in order to communicate three-dimensional information in the manner of a two-plane projection technique, for example.

It is noted that additional embodiments of the representations are fundamentally also conceivable wherein, for example, additional geometric parameters are shown that can result from the bearing of instrument and target position/target region. In particular, in the second exemplary embodiment of the method according to the invention it is additionally conceivable to also incorporate into the representation the three-dimensional high-contrast image data set that that has already been reconstructed. Finally, it is possible to simultaneously use low-contrast image data and a position determination device.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for graphically assisting navigation of a medical instrument in a magnetic resonance device within a medical procedure region in a patient in the magnetic resonance device, comprising:
   - operating the magnetic resonance device with the patient therein to obtain a high-contrast image data set representing said procedure region, said high-contrast image data set being acquired in a magnetic resonance device coordinate system associated with the magnetic resonance device;
   - supplying said high-contrast image data set to a computerized processor and, in said computerized processor, automatically determining, from said high-contrast image data set, coordinates of a target, in said magnetic resonance device coordinate system, to be reached by the instrument in said procedure region, said coordinates of said target being selected from the group consisting of a target position and a target region;
   - obtaining instrument-representing data representing said instrument during movement of said instrument in said procedure region toward said target by operating said magnetic resonance device to intermittently or continuously acquire low-contrast image data representing said instrument during movement of said instrument in said procedure region toward said target;
   - supplying said low contrast data representing said instrument to said computerized processor and, in said processor, automatically generating a low-contrast image therefrom in which said instrument, and said target at said coordinates of said target, are visualized; and
   - at a display device in communication with said computerized processor, visually displaying said low-contrast image to show said instrument relative to said coordinates of said target.

2. A method as claimed in claim 1 comprising representing said target at said display with a symbolic marking indicating an orientation of said target.

3. A method as claimed in claim 2 comprising presenting a representation at said display comprising a slice image of said low-contrast data, and entering said symbolic marking into said slice image when reconstructing said slice image.

4. A method as claimed in claim 2 comprising employing, as said symbolic marking, an indicator representing information identifying a distance of the target position perpendicular to the slice plane.

5. A method as claimed in claim 4 wherein said indicator has a shape, a color, and a size, and comprising configuring at least one of said shape and said color of said indicator to indicate a position of the target above or below the plane of the slice image, and indicating the distance of the target from the plane of the slice by said size of said indicator.

6. A method as claimed in claim 1 comprising forming said low-contrast image data from two slice images.

7. A method as claimed in claim 6 wherein said two slice images are substantially perpendicular to each other.

8. A method as claimed in claim 1 comprising incorporating at least one additional subject or area in said representation, having known coordinates in said high-contrast image data set.

9. A method as claimed in claim 1 comprising, in said computerized processor, automatically determining at least one of an estimated future position and a movement line of said instrument from said position and orientation of said instrument, and incorporating a representation of at least one of said estimated future position and said movement line in said representation at said display.

10. A method as claimed in claim 1, comprising determining geometric parameters in said computerized processor that characterize said instrument relative to said target, and incorporating said geometric parameters in said representation at said display.

11. A method as claimed in claim 1 comprising, in said processor, automatically determining, from said instrument-representing data, a position and an orientation of said instrument relative to the coordinate system of the magnetic resonance device during said movement, and representing said position and orientation of said instrument relative to said coordinates of said target in the low-contrast image displayed at said display device.

* * * * *